Figure 1:
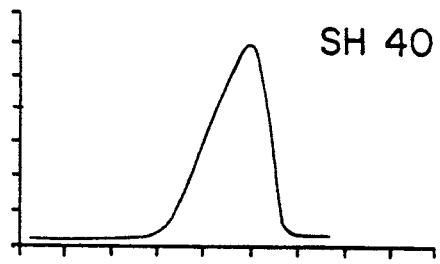

United States Patent [19]

Conti et al.

[11] Patent Number: 5,164,378
[45] Date of Patent: Nov. 17, 1992

[54] SUPERSULFATED HEPARINS

[75] Inventors: Renato Conti; Paolo Casati; Maria B. Gorini; Antonio Maggi, all of Milan, Italy

[73] Assignee: Iketon Farmaceutici, S.r.l., Milan, Italy

[21] Appl. No.: 618,051

[22] Filed: Nov. 26, 1990

[30] Foreign Application Priority Data

Nov. 24, 1989 [IT] Italy ............... 22504 A/89

[51] Int. Cl.$^5$ .................... A61K 31/725; C08B 39/10
[52] U.S. Cl. ........................ 514/56; 514/54; 536/21; 536/54; 536/55.1; 536/55.3; 536/122
[58] Field of Search ............ 514/56, 54; 536/21, 536/553, 124, 54, 55.1, 122

[56] References Cited

U.S. PATENT DOCUMENTS

| | | |
|---|---|---|
| 3,506,642 | 4/1970 | Koh et al. ............... 536/21 |
| 4,727,063 | 2/1988 | Naggi et al. ............ 536/21 |
| 4,757,057 | 7/1988 | Fussi et al. ............. 514/56 |
| 4,948,881 | 8/1990 | Naggi et al. ............ 536/20 |
| 4,966,894 | 10/1990 | Herr et al. ............. 514/56 |
| 4,990,502 | 2/1991 | Lormeau et al. ........ 514/56 |
| 5,008,247 | 4/1991 | Meinetsberger ........ 514/25 |
| 5,013,724 | 5/1991 | Petitou et al. .......... 536/21 |

FOREIGN PATENT DOCUMENTS

| | | |
|---|---|---|
| 0058397 | 8/1982 | European Pat. Off. ........ 514/56 |
| 0116251 | 8/1984 | European Pat. Off. ........ 536/21 |
| 0133078 | 2/1985 | European Pat. Off. ........ 536/21 |
| 0287477 | 10/1988 | European Pat. Off. ........ 536/21 |
| 3244214 | 5/1984 | Fed. Rep. of Germany .... 536/21 |
| 60-49001 | 3/1985 | Japan ......................... 536/21 |
| 8912070 | 12/1989 | World Int. Prop. O. ....... 536/21 |

OTHER PUBLICATIONS

Nagasawa et al; Carbohydrate Research 18:95–102 (1971).

Primary Examiner—Ronald W. Griffin
Assistant Examiner—Nancy S. Carson
Attorney, Agent, or Firm—Mathews, Woodbridge & Collins

[57] ABSTRACT

A process for the depolymerization and supersulfation of heparin and the so obtained supersulfated heparins are disclosed. The process comprises treating heparin with oleum containing from 2 to 6% free sulfuric anhydride at a temperature from −10° to +20° C. The obtained heparins have molecular weights from 2000 to 5000 and a sulfation degree from 3.4 to 4.3. All of them are endowed with a remarkable antithrombotic activity.

12 Claims, 1 Drawing Sheet

SUPERSULFATED HEPARINS

DISCLOSURE OF THE INVENTION

The present invention relates to low molecular weight supersulfated heparins, to the pharmaceutically acceptable salts thereof, to a process for the preparation thereof, and to pharmaceutical compositions containing super sulfated heparins or salts as active ingredients.

U.S. Pat. No. 4,727,063 discloses low molecular weight heparins having a sulfation degree of at least 2.5 and a molecular weight ranging from 2000 to 9000, prepared by depolymerization and sulfation with a mixture of sulfuric and chlorosulfonic acid. None has a sulfation degree up to 3.5.

EPA 214,879 discloses a process for the sulfation of glycosaminoglycanes (GAG) in which a certain GAG is transformed into a soluble salt in a specific organic solvent, and the solution is treated with a conventional sulfating reagent. The above process, allows to obtain supersulfated GAGs without causing depolymerization, but the disclosed supersulfated GAGs, except for a disaccharide, have a sulfation degree that never exceeds 3.41.

U.S. Pat. No. 3,454,560 discloses a process for the depolymerization and sulfation of chondroitin sulfate by means of sulfuric acid at a concentration not lower than 85% w/w. The sulfuric acid can contain another sulfating agent, such as sulfuric anhydride or chlorosulfonic acid, but the same document specifies that, even operating in said ambient, only sulfuric acid participates in the sulfation reaction.

It has been found that in case of heparin, it is possible to obtain a low molecular weight supersulfated heparin by reacting the heparin with oleum. The sulfuric anhydride contained in oleum is necessary for the sulfation and the use of sulfuric acid only results either in depolymerization without remarkable sulfation, or in complete degradation.

It has also been found that by reaction with oleum new low molecular weight supersulfated heparins are obtained which have a molecular weight within a relatively short range and a sulfation degree higher than those of all previously described supersulfated heparins.

It has been found that new low molecular weight supersulfated heparins obtained from heparin by reacting with oleum have a markedly reduced anticoagulant activity, a very good antithrombotic activity and a lipoproteinlipasic activity substantially higher than those of previously known low molecular weight heparins.

Finally, it has surprisingly been found that the low molecular weight supersulfated heparins of the present invention, contrary to heparin and products of U.S. Pat. No. 4,727,063, are powerful thrombin inhibitors.

Hence the present invention, according to one of its aspects, relates to new low molecular weight supersulfated heparins consisting of mixtures of heparinic components having the following features:
  molecular weight from about 2000 to about 5000 Daltons.
  sulfation degree, expressed as sulfate/carboxylate ratio, from 3.5 to 4.5,
  direct antithrombin activity, not mediated by Antithrombin III and to the pharmaceutically acceptable salts thereof.

Among the low molecular weight supersulfated heparins of the present invention, those having molecular weights between 2900 and 4500 are particularly advantageous and those with molecular weights between 3000 and 4000 are preferred. Among these latter, a mixture of heparinic components, having mean molecular weight of 3300, is endowed with particular properties. Molecular weight was determined by Gel Permeation Chromatography in HPLC on a TSK SW 2000 column.

The low molecular weight supersulfated heparins of the present invention show an absorbance maximum in the UV spectrum at 312 nm. The presence of such a maximum is a peculiar characteristic of the products of the present invention, as neither heparin nor the products disclosed in U.S. Pat. No. 4,727,063 have it. Such a maximum was determined in an aqueous solution containing 10 mg/ml of said heparins.

Regarding elemental analysis, the low molecular supersulfated heparins of the present invention have a carbon/nitrogen ratio (C/N) from 11.7 to 12.1 (on a molar basis) and a carbon/sulfur ratio (C/S) from 2.5 to 2.9.

The sulfation degree of low molecular weight supersulfated heparins of the present invention is preferably at least 3.6 and it ranges from 3.6 to 4.5, preferably from 3.65 to 4.3.

According to another of its aspects, the present invention concerns a process for the preparation of low molecular weight supersulfated heparins having molecular weights from 2000 to 5000 and a sulfation degree between 3.5 and 4.5, which process comprises treating heparin with oleum at a temperature between $-10°$ and $30°$ C.

The heparin used as the starting material can be standard heparin or any other commercially available heparin, provided that it has a good quality. Generally a sodium salt of heparin is used, even if other salts can conveniently be used. It is preferable that starting heparin be anhydrous, hence a preliminary dehydratation is properly performed, for example, at a temperature of around 50° to 60° C.

The oleum used for the depolymerization and sulfation reaction preferably contains from 2 to 7% free sulfuric anhydride. It is prepared extemporarily by adding 20% sulfuric anhydride oleum to concentrated sulfuric acid till the complete conversion of water into sulfuric acid and in the presence of the desired amount of free sulfuric anhydride.

The concentration of heparin in oleum may range from about 5 to about 20% w/v. In practice, it is advisable to use from 5 to 15 ml of oleum for each gram of heparin.

The reaction time ranges from a few minutes to more than one hour and obviously depends on the temperature. In practice it is possible to operate at a temperature from $-10°$ to $+30°$ C. for a time ranging from 5–10 minutes to 75 minutes.

The desired final product is recovered with known processes, neutralizing the sulfuric acid with an alkali base, preferably sodium hydroxide and, after removing the so obtained sulfate salts, separating the low molecular weight supersulfated heparin by dialysis and optional subsequent lyophilization.

Particularly interesting products are prepared by subjecting the desalinized product to gel filtration, so to obtain supersulfated heparins with a very narrow molecular weight distribution and a better defined pharmacological activity.

The low molecular weight supersulfated heparin is isolated as the salt of the employed alkali hydroxide, preferably the sodium salt. The salt can be transformed into another one, for instance into the calcium salt, by an exchange reaction using a ion-exchange resin.

Amino acid salts are very interesting, in particular those of lysine and arginine. These salts are obtained first passing the sodium salt through a cationic exchange column, for instance Amberlite IR 120 in the acid form, at low temperature (about 5° C.), collecting the eluate directly in an aqueous solution of the amino acid and isolating the salt by lyophilization.

Compared to the known processes for the supersulfation of heparin, the process of the present invention has remarkable advantages. More in detail, compared to the process disclosed in EPA 214,879, the process of the invention employs no organic solvents and accordingly does not need solvents elimination or solvent recovery steps. Moreover, the process of the invention can use commercial heparin directly without transforming it into an organic solvent soluble salt. Compared to the process disclosed in U.S. Pat. No. 4,727,063, the process of the invention causes no evolution of gases nor foam formation, as in known processes. In addition the process of the present invention differs from that of U.S. Pat. No. 4,727,063 in that the presence of water in the reaction medium is there critical and controls the depolymerization degree. In the process of the present invention, the reaction environment is strictly anhydrous.

The low molecular weight supersulfated heparins of the present invention have extremely interesting pharmacological properties, better and qualitatively different from all of the corresponding products described in the prior art.

More particularly, the new products of the present invention show an extremely reduced anticoagulant activity, far less than that of heparin. According to the USP in vitro method, the low molecular weight supersulfated heparins of the present invention have an activity of 18–22 IU/mg, while commercial injectable heparins have an activity of 175–180 IU/mg, about ten times higher.

On the other hand, the antithrombotic activity of the low molecular weight supersulfated heparins of the present invention is substantially identical to that of heparin, according to stasis-induced thrombosis test in the jugular vein of the rabbit (NIADA R. et al. Pharmac. Res. Commun. 11, 349, 1979).

Moreover, compared to heparin, the low molecular weight supersulfated heparins of the present invention have the advantage to be less liable to cause hemorrhages, as proved in the bleeding time test in the rat (DEJANA et al. Thromb. Haemost. 48, 108, 1982) from which the products of the present invention show an activity more than ten times lower.

The low molecular weight supersulfated heparins of the present invention also have an extremely high lipoproteinlypasic activity, by far higher than the activity of heparin and low molecular weight supersulfated heparins previously known.

The lipoproteinlipasic activity of a representative product of the present invention, called SH-40/1 (see Example 1), was determined in the rabbit plasma after subcutaneous administration. This activity was compared to that of a commercial sodium heparin (Diosynth lot 1334) and to that of a product prepared as disclosed in Example 1 of U.S. Pat. No. 4,727,063 (AH-16, sulfation degree 3.0). The examined products were administered to New Zealand rabbits, weighing 2.6–2.8 kg which were fastened overnight. Blood withdrawals were carried out in citrate at 0, 30, 60, 90, 120, 180, and 240 minutes post administration.

The lipoproteinlipasic activity was evaluated by dosing the free fatty acids released from the plasma incubation with a substrate containing triglycerides (Intralipid). In this test, the product SH-40/1 was ten times more active than heparin and two times more active than the reference product AH-16.

The low molecular weight supersulfated heparins of the present invention, and particularly those obtained after fractionating, are direct thrombin inhibitors, another surprising and peculiar property. This property was evaluated in the amidolytic activity in vitro test on human thrombin either in the absence or in the presence of antithrombin III (AT III). Thrombin acts on a synthetic substrate Chromozym TH-Boehringer (Tosyl-Glu-Pro-Arg-p-nitroanilide), releasing p-nitroaniline which has a strong absorbance at 405 nm. Optical density variation at 405 nm (OD 405) is proportional to the amount of thrombin in the test. In the presence of inhibitors, the $OD_{405}$ variation is reduced. Heparin shows poor direct thrombin inhibition but a strong inhibition in the presence of AT III. but supersulfated heparin of U.S. Pat. No. 4,727,063, shows strong direct thrombin inhibition which increases in the presence of AT III. The product of the present invention produces strong direct inhibition of thrombin but inhibition does not increase in the presence of AT III. Hence, the low molecular weight supersulfated heparins of the present invention do not have affinity for AT III.

The low molecular weight supersulfated heparins of the present invention have an extremely low toxicity and are well tolerated either when administered by either the oral or parenteral route. Hence they constitute valuable active ingredients for drugs useful as antithrombotic and antiatherosclerotic agents. Particularly, their high lipoproteinlipasic activity makes them extremely interesting potential antihyperlipemic agents.

According to another of its aspects, the present invention provides pharmaceutical compositions containing, as active ingredients, the low molecular weight supersulfated heparins of the invention.

The pharmaceutical compositions of the present invention can be formulated for the oral, sublingual, subcutaneous, intravenous, transdermic or rectal administrations in dosage units and in admixture with pharmaceutical excipients or vehicles. Convenient dosage forms include, among those for oral administration, tablets, powders, granulates, and, among those for parenteral administration, solutions especially for subcutaneous, intramuscular or intravenous administrations.

The pharmaceutical compositions of the present invention are administered, in the above mentioned forms and routes, to animals and man in case of a pathological increase in thrombin and lipids, particularly in the prevention of thrombosis and in the treatment of atherosclerosis.

The daily amount in the aforesaid indications may range from 0.1 to 100 mg/kg and each unitary dose may contain from 1 to 1000 mg of the active ingredient. Such unitary dose can be administered from 1 to 3 times a day for the treatment of coagulation, lipidic metabolism disorders and atherosclerosis.

Figure 2:
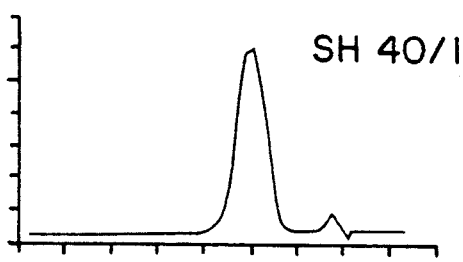
Figure 3:
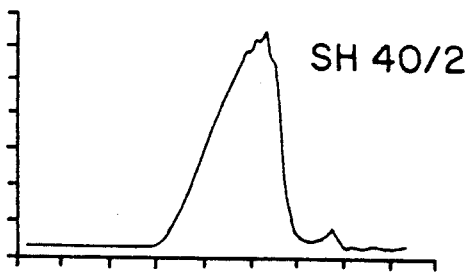
Figure 4:
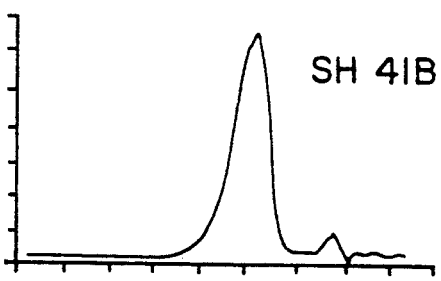
Figure 5:
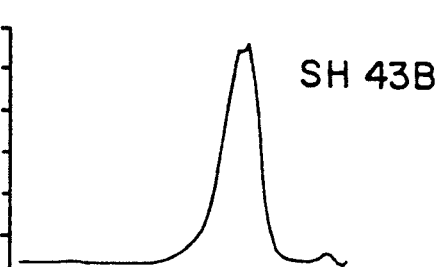

The following examples further illustrate the invention. HPLC profiles of the obtained products, SH 40, SH 40/1, SH 40/2, SH 41B, SH 43B, are shown in FIGS. 1, 2, 3, 4, and 5, respectively.

EXAMPLE 1

50 g of sodium heparinate (from swine mucosa—Diosynth lot 1334), vacuum dried at 60° C. for 65 hours, are added under strong stirring to 400 ml of 4% $SO_3$ oleum kept at +5° C. After 10 minutes of stirring at +5° C., the temperature is gradually raised to +20° C. and maintained for 30 minutes. The reaction mixture is then dropped into 5 l of cold water (2°-3° C.), adding at the same time, a 30% sodium hydroxide solution (w/v) mantaining pH between 5 and 9. The solution is kept at 2°-3° C. overnight and the crystallized sodium sulfate is separated by vacuum filtration.

The filtrate (about 7 l) is desalted by ultrafiltration (Amicon DC 10 LA with membrane S 10 Y3, cut off 3000), concentrated by ultrafiltration and lyophilized. 47.4 g of the product (SH 40) are obtained, 94.81% yield, having the following characteristics:

| elemental analysis | C 15.68% |
| | H 2.93% |
| | N 1.56% |
| | S 16.48% |
| sulfate/carboxylate ratio | 4.30 |
| mean molecular weight | 4100 Daltons |

EXAMPLE 2

5 g of sodium heparinate (from swine mucosa—Diosynth lot 1334), vacuum dried at 60° C. for 48 hours, are added under strong stirring to 35 ml of 2% $SO_3$ oleum kept at +10° C.

The suspension is stirred for 5 minutes at 10° C. and then temperature is raised to 25° C., stirring for further 25 minutes. The solution is then neutralized, dropping it slowly into 500 ml of water cooled at 2°-3° C., which, at the same time is added with a 30% sodium hydroxide solution, adjusting pH between 5 and 9. After separation of the crystallized sodium sulfate, the solution is concentrated under vacuum and, after elimination of other sodium sulfate, it is charged on a Sephadex G 50 (K50/100) column equilibrated with NaCl 0.3M. The first 1000 ml of eluate are discharged and the further 250 ml are collected, which are desalted and concentrated in ultrafilter Amicon 8400 cell on YM2 membrane (cut off 1000).

By lyophilization 1.8 g of product (SH 40/1) are obtained 36.16% yield, having the following characteristics:

| elemental analysis | C 15.48% |
| | H 2.89% |
| | N 1.53% |
| | S 16.33% |
| sulfate/carboxylate ratio | 4.24 |
| mean molecular weight | 3300 Daltons |

EXAMPLE 3

5 g of sodium heparinate (from swine mucosa—Diosynth lot 1334), vacuum dried at 60° C. for 48 hours, are added to 35 ml of 2% $SO_3$ oleum kept at −5° C.

After stirring for 15 minutes at −5° C., the temperature is raised and kept to 20° C. for 60 minutes. The reaction mixture is neutralized dropping it slowly into 500 ml of ice-water, at the same time adding thereto a 30% sodium hydroxide solution, maintaining pH between 5 and 9. The solution is cooled (4°-5° C.) overnight and, after the separation of the crystallized sodium sulfate, it is concentrated under vacuum to 60 ml and dialyzed against water in dialysis bags SPECTRAPOR 1 (cut off 6000-8000). Finally the solution is concentrated under vacuum and lyophilized. 5.5 g of product (SH 40/2) are obtained, yield 110%, having the following characteristics:

| elemental analysis | C 15.71% |
| | H 2.99% |
| | N 1.55% |
| | S 16.63% |
| sulfate/carboxylate ratio | 4.23 |
| mean molecular weight | 3500 Daltons |

EXAMPLE 4

35 g of sodium heparinate (from swine mucosa—Diosynth lot 1334), vacuum dried at 60° C. for 48 hours, are added to 400 ml of 3.5% $SO_3$ oleum kept at +10° C.

After stirring for 5 minutes at +10° C. the temperature is raised and kept to +25° C. for 30 minutes. The reaction mixture is neutralized dropping it into 5 l of ice-water, to which a 30% (w/v) sodium hydroxide solution is added at the same time. After the separation of sodium sulfate, which crystallizes at +5° C., the solution (about 7 l) is ultrafiltered with ultrafilter AMICON DC 10 LA with spiral cartridge S 10 Y3, cut off 10.000. The permeate is concentrated using the same ultrafilter and a S 10 Y3 membrane with cut off 3000, washed till complete elimination of sodium sulfate and lyophilized. 12.95 g of product (SH 41 B) are obtained, yield 37%, having the following characteristics:

| elemental analysis | C 16.97% |
| | H 3.26% |
| | N 1.69% |
| | S 16.19% |
| sulfate/carboxylate ratio | 3.65 |
| mean molecular weight | 3650 Daltons |

EXAMPLE 5

50 g of sodium heparinate (from swine mucosa—Diosynth lot 1334), vacuum dried at 60° C. for 48 hours, are added to 400 ml of 2.5% $SO_3$ oleum kept at −5° C.

After stirring for 20 minutes at −5° C. the temperature is raised and kept to +20° C. for 50 minutes, then it is lowered to +5° C. again and the reaction mixture is neutralized dropping it in 5 l of ice-water, to which a 30% (w/v) sodium hydroxide solution is added at the same time. The reaction is then carried out like in example 4. 25.4 g of product (SH 43 B) are obtained, yield 50.29%, having the following characteristics:

| elemental analysis | C 17.22% |
| | H 3.22% |
| | N 1.67% |
| | S 15.88% |
| sulfate/carboxylate ratio | 3.85 |
| mean molecular weight | 4100 Daltons |

EXAMPLE 6

5 g of the product obtained as disclosed in example 3 are dissolved in 200 ml of distilled water and converted into the acid form by passing through 400 ml of ion-exchange resin IR 120 H+ in a chromatographic column cooled at 5° C. The obtained solution is neutralized with 640 mg of calcium hydroxide suspended in 10 ml of distilled water and it is lyophilized. 5.14 g of product consisting of supersulfated heparin, calcium salt, are obtained.

EXAMPLE 7

5 g of the product obtained as disclosed in example 3 are dissolved in 200 ml of distilled water and converted into the acid form by passing through 400 ml of ion-exchange resin IR 120 H+ in a chromatographic column cooled at 5° C. The obtained solution is neutralized with 2.64 g of Arginine base and lyophilized. 7.58 g of product consisting of supersulfated heparin, arginine salt, are obtained.

EXAMPLE 8

5 g of the product obtained as disclosed in example 3 are dissolved in 200 ml of distilled water and converted into the acid form by passing through 400 ml of ion-exchange resin IR 120 H+ in a chromatographic column cooled at 5° C. The obtained solution is neutralized with 2.76 g of lysine base and lyophilized. 7.6 g of product consisting of supersulfated heparin, lysine salt, are obtained.

EXAMPLE 9

100 g of sodium heparinate (from swine mucosa—Diosynth lot 1583), vacuum dried at 60° C. for 48 hours, are added under strong stirring to 400 ml of 2% $SO_3$ oleum kept at +12° C.

The suspension is stirred for 5 minutes at +12° C. and then temperature is raised to 25° C. and kept under stirring for further 25 minutes. The solution is then neutralized dropping it into 10 l of ice-water, a 30% sodium hydroxide solution is added thereto at the same time, maintaining pH between 5 and 9. The neutralized solution, whose final pH is 6.7, is left at 5° C. overnight. Sodium sulfate, which separates by crystallization, is eliminated by vacuum filtration, and the filtrate, about 20 l, is concentrated and desalted in ultrafilter Amicon DC 10 with spiral cartridge S 10 Y3 (cut off 3000).

The concentrated solution (500 ml) is then chromatographed on Amicon Column G 180×1000 containing 25 l of a Sephadex G 50 (Pharmacia) column equilibrated with 0.3M NaCl. The first 7500 ml of eluate are discharged and the further 4500 ml are collected, concentrated and desalted in ultrafilter Amicon 2000 cell on YM2 membrane (cut off 1000).

500 ml of solution are obtained, which by lyophilization give 35 g of product (SH 14 D), having the following characteristics:

| | |
|---|---|
| elemental analysis | C 16.85% |
| | H 2.39% |
| | N 1.63% |
| | S 16.50% |
| sulfate/carboxylate ratio | 4.33 |
| mean molecular weight | 3456 Daltons |

We claim:
1. A composition of matter selected from the group consisting of
   (a) low molecular weight supersulfated heparin derivatives having (i) a molecular weight of from about 2000 to about 5000 Daltons; (ii) a sulfation degree of from 3.5:1 to 4.5:1 sulfate groups:carboxy groups; and (iii) direct antithrombin activity not mediated by Antithrombin III; and
   (b) a pharmaceutically acceptable salt thereof.
2. A composition of matter according to claim 1 wherein the molecular weight is from 2900 to 4500 Daltons.
3. A composition of matter according to claim 2 wherein the molecular weight is from 3000 to 4000 Daltons.
4. A composition of matter according to claim 3 wherein the molecular weight is about 3300 Daltons.
5. A composition of matter according to claim 1 wherein the sulfation degree is 3.6:1 to 4.5:1.
6. A composition of matter according to claim 5 wherein the sulfation degree is from 3.65:1 to 4.3:1.
7. A composition of matter according to claim 1 demonstrating an absorbance maximum at 312 nm, measured as a 10 mg/ml aqueous solution.
8. A composition of matter according to claim 1 wherein the pharmaceutically acceptable salt is the sodium, calcium, arginine, or lysine salt.
9. A pharmaceutical composition comprising an effective amount of a composition of matter according to claim 1 in combination with a pharmaceutically acceptable carrier.
10. A pharmaceutical composition according to claim 9 containing from 0.1 to 1000 mg of said composition of matter in dosage unit form.
11. A process for the preparation of a composition of matter according to claim 1 which comprises allowing anhydrous heparin to react with oleum containing from 2 to 7% free sulfuric anhydride at temperatures of from −10° to 30° C. at least until a sulfation degree of from 3.5:1 to 4.5:1 is obtained.
12. A process according to claim 11 wherein the ratio of anhydrous heparin to oleum is from about 5% to about 20% w/v.

* * * * *